(12) United States Patent
Cabeza-Guillen et al.

(10) Patent No.: US 9,055,890 B2
(45) Date of Patent: Jun. 16, 2015

(54) EYEGLASS PRESCRIPTION METHOD

(75) Inventors: Jesus-Miguel Cabeza-Guillen, Aalen (DE); Timo Kratzer, Aalen (DE)

(73) Assignee: Carl Zeiss Vision GmbH, Aalen (DE)

( * ) Notice: Subject to any disclaimer, the term of this patent is extended or adjusted under 35 U.S.C. 154(b) by 81 days.

(21) Appl. No.: 13/302,529

(22) Filed: Nov. 22, 2011

(65) Prior Publication Data

US 2012/0069297 A1 Mar. 22, 2012

Related U.S. Application Data

(62) Division of application No. 11/835,109, filed on Aug. 7, 2007, now Pat. No. 8,079,707.

(60) Provisional application No. 60/854,374, filed on Oct. 25, 2006.

(51) Int. Cl.
*A61B 3/10* (2006.01)

(52) U.S. Cl.
CPC .................................... *A61B 3/1015* (2013.01)

(58) Field of Classification Search
CPC .. A61B 3/1015; G02C 2202/22; G02C 7/028; G02C 7/027
USPC .......................................... 351/200, 205, 246
See application file for complete search history.

(56) References Cited

U.S. PATENT DOCUMENTS

| | | | |
|---|---|---|---|
| 4,105,302 A | 8/1978 | Tate | |
| 6,048,064 A | 4/2000 | Hosoi | |
| 6,382,795 B1 | 5/2002 | Lai | |
| 6,406,146 B1 | 6/2002 | Lai | |
| 6,511,180 B2 | 1/2003 | Guirao et al. | |
| 6,575,572 B2 | 6/2003 | Lai et al. | |
| 6,688,745 B2 | 2/2004 | Ross | |
| 6,997,555 B2 | 2/2006 | Dick et al. | |
| 7,029,119 B2 | 4/2006 | Youssefi | |
| 7,084,986 B2 | 8/2006 | Hellmuth et al. | |
| 7,547,102 B2 | 6/2009 | Dai | |
| 2001/0016695 A1* | 8/2001 | Mihashi et al. | 600/558 |
| 2003/0038921 A1 | 2/2003 | Neal | |

(Continued)

FOREIGN PATENT DOCUMENTS

| | | |
|---|---|---|
| CN | 1291281 | 4/2001 |
| DE | 601 21 123 | 2/2007 |

(Continued)

OTHER PUBLICATIONS

Written Opinion of the International Searching Authority, for the corresponding PCT Application No. PCT/EP2007/008524, filed Oct. 1, 2007.

(Continued)

*Primary Examiner* — Mahidere Sahle
(74) *Attorney, Agent, or Firm* — Fish & Richardson P.C.

(57) ABSTRACT

In general, in some embodiments, the disclosure provides a method that includes making a subjective refraction of a person to determine information about the person's vision, making a wavefront measurement of one or both of the person's eyes to determine information about the optical properties of one or both of the person's eyes (e.g., aberrations), calculating a prescription for the person based on the information about the person's vision and the information about the optical properties of one or both of the person's eyes, and outputting the prescription.

23 Claims, 4 Drawing Sheets

(56) References Cited

U.S. PATENT DOCUMENTS

| | | |
|---|---|---|
| 2004/0008323 A1 | 1/2004 | Williams |
| 2004/0100619 A1 | 5/2004 | Olivier |
| 2004/0169820 A1 | 9/2004 | Dai et al. |
| 2005/0174535 A1 | 8/2005 | Lai et al. |
| 2005/0179861 A1 | 8/2005 | Kitani et al. |
| 2006/0023162 A1 | 2/2006 | Azar et al. |
| 2006/0197911 A1 | 9/2006 | Williams |
| 2006/0279699 A1 | 12/2006 | Liang |
| 2008/0100800 A1 | 5/2008 | Guillen et al. |
| 2009/0015787 A1 | 1/2009 | Guillen et al. |
| 2009/0079940 A1 * | 3/2009 | Dai et al. .................. 351/246 |

FOREIGN PATENT DOCUMENTS

| | | |
|---|---|---|
| EP | 1 324 689 | 8/2006 |
| WO | WO 01/89372 | 11/2001 |
| WO | WO 02/083078 | 10/2002 |
| WO | WO 2004/072687 | 8/2004 |
| WO | WO 2004/096014 | 11/2004 |
| WO | WO 2006/009909 | 1/2006 |

OTHER PUBLICATIONS

The International Search Report for corresponding PCT Application No. PCT/EP2007/008524, mailed May 21, 2008.

EP Office Action for the corresponding EP Application No. 07 818 604.6, dated Aug. 17, 2009.

Power Point presentation entitled "A tutorial on higher order aberrations: What are they? How are they measured? What is their clinical relevance? Can they be corrected?," presented by Louis J. Catania, O.D., F.A.A.O., 2003.

Power Point presentation entitled "A tutorial on higher order aberrations," by Louis J. Catania, (C) 2004 by Nicolitz Eye Consultants.

Power Point presentation entitled "Clinical Results for Wavefront Corrected Spectacle Lenses," by Perry S. Binder, (C) 2004 by Ophthonix.

Power Point presentation entitled "Vision Optimized Spectacles and Contact Lenses," presented by Jerome A. Legerton, OD, MS, MBA, FAAO, 2004.

Chinese Office Action with English translation, for the corresponding Chinese Application No. 2007/80040137.8, dated Apr. 14, 2010.

English translation of Chinese Office Action for the corresponding CN Application No. 200780040137.8, dated Dec. 7, 2011.

Chinese Office Action with English translation, for the corresponding Chinese Application No. 200780040137.8, dated Jul. 2, 2012.

Chinese Notification of Reexamination, with translation thereof, for CN Appl No. 200780040137.8, dated May 4, 2014.

Chinese Office Action, with translation thereof, for CN Appl No. 200780040137.8, dated Nov. 15, 2014.

* cited by examiner

EYEGLASS PRESCRIPTION METHOD

CROSS-REFERENCE TO RELATED APPLICATION

This application is a divisional of U.S. Ser. No. 11/835,109, filed Aug. 7, 2007, which claims priority under 35 U.S.C. §119(e)(1) to U.S. Ser. No. 60/854,374, filed Oct. 25, 2006. The entire contents of these applications are hereby incorporated by reference.

FIELD

Eyeglass prescription methods, and related systems, components and articles are disclosed.

BACKGROUND

Eye care professionals (ECPs), such as opticians, optometrists, ophthalmologists, and eye doctors, typically dispense eye glasses to people based on a study of the person's vision that involves taking a medical history of the person's vision and a subjective refraction to get the person's prescription. After the person selects eyeglass frames, the ECP usually measures the centration of the frame for the person and orders lenses for the frame based on the person's prescription and the centration measurement.

SUMMARY

In general, methods for dispensing eyeglasses are disclosed. The methods can involve making a subjective refraction and an objective refraction and combine both refractions to calculate the person's prescription. The methods may involve making a wavefront measurement of one or both of the person's eyes and using the wavefront measurement to calculate the person's prescription.

In general, in one aspect, the disclosure features a method that includes making a subjective refraction of a person to determine information about the person's vision, and making an objective refraction of the person to determine information about the person's vision. The method also includes calculating a prescription for the person based on the information about the person's vision determined by the subjective refraction and the objective refraction, and outputting the prescription.

In general, in another aspect, the disclosure features a system that includes an input interface configured to input information about a person's vision determined on the basis of a subjective refraction. The system also includes a device configured to get information about a person's vision determined on the basis of an objective refraction. The system further includes a calculating device configured to calculate a prescription for the person based on the information about the person's vision determined by subjective refraction and based on the information about the person's vision determined by objective refraction. In addition, the system includes an outputting interface configured to output the prescription.

In general, in a further aspect, the disclosure features a method that includes making a subjective refraction of a person to determine information about the person's vision. The method also includes making a wavefront measurement of one or both of the person's eyes to determine information about the optical properties of one or both of the person's eyes. The method further includes calculating a prescription for the person based on the information about the person's vision and the information about the optical properties of one or both of the person's eyes. In addition, the method includes outputting the prescription.

In general, in an additional aspect, the disclosure features a method that includes making a wavefront measurement of one or both of the person's eyes to determine information about the optical properties of one or both of the person's eyes. The method also includes calculating a prescription for the person based on the information about the optical properties of one or both of the person's eyes, where calculating the prescription includes ray tracing light paths through one or both of the person's eyes based on the information about the optical properties of one or both of the person's eyes. The method further includes outputting the prescription.

In general, in another aspect, the disclosure features a system that includes relay optics configured to collect illumination scattered from a person's eye during operation of the system. The system also includes an optical sensor configured to detect the illumination collected by the relay optics. The system further includes an electronic processor configured to receive information about the illumination detected by the optical sensor and to calculate a prescription for the person based on the information, where calculating the prescription includes ray tracing light paths through the person's eye based on the information.

In general, in another aspect, the disclosure features a method that includes calculating a prescription for the person based on the information about a person's vision determined by a subjective refraction and an objective refraction.

In general, in a further aspect, the disclosure features a system that includes a device configured to calculate a prescription for a person based on information about the person's vision determined by subjective refraction and based on information about the person's vision determined by objective refraction. The system also includes an outputting interface configured to output the prescription.

In general, in a further aspect, the disclosure features a method that includes making a subjective refraction of a person to determine information about the person's vision, making a wavefront measurement of one or both of the person's eyes to determine information about the optical properties of one or both of the person's eyes (e.g., aberrations), calculating a prescription for the person based on the information about the person's vision and the information about the optical properties of one or both of the person's eyes, and outputting the prescription.

In general, in another aspect, the disclosure features a method that includes making a wavefront measurement of one or both of the person's eyes to determine information about the optical properties of one or both of the person's eyes, calculating a prescription for the person based on the information about the optical properties of one or both of the person's eyes (e.g., aberrations), wherein calculating the prescription includes ray tracing light paths through one or both of the person's eyes based on the information about the optical properties of one or both of the person's eyes (e.g., using ray tracing software), and outputting the prescription.

In general, in still another aspect, the disclosure features a system that includes an input interface configured to input information about a person's vision determined on the basis of a subjective refraction, a device configured to get information about a person's vision determined on the basis of an objective refraction (e.g. via a wavefront refractor such as a Shack-Hartmann sensor, an auto-refractor, or a tomograph etc.), a calculating device, such as a personal computer or a workstation, configured to calculate a prescription for the person based on the information about the person's vision determined by subjective refraction and based on the information about the person's vision determined by objective refraction, and an outputting interface configured to output the prescription.

In general, in another aspect, the disclosure features a system that includes relay optics (e.g., imaging optics and/or interferometer optics) configured to collect illumination scattered from a person's eye during operation of the system, an optical sensor (e.g., a Hartmann-Shack sensor) configured to detect the illumination collected by the relay optics, and electronic processor (e.g., a computer) configured to receive information about the illumination detected by the optical sensor and to calculate a prescription for the person based on the information. Calculating the prescription includes ray tracing light paths through the person's eye based on the information.

In general, in still another aspect, the disclosure features a system that includes an input interface configured to input information about the person's vision determined on the basis of a subjective refraction of a person, a wavefront measurement device configured to make a wavefront measurement of one or both of the person's eyes to determine information about the optical properties of one or both of the person's eyes, a calculating device configured to calculate a prescription for the person based on the information about the person's vision and the information about the optical properties of one or both of the person's eyes; and an output interface configured to output the prescription.

Embodiments of the methods and systems can include one or more of the following features.

The objective refraction may be derived from a wavefront measurement of one or both of the person's eyes. The wavefront measurement can acquire information about the optical properties of one or both of the person's eyes. A wavefront measurement may be accomplished by the Shack-Hartmann method or the Tscherning method.

In some embodiments, the objective refraction may also be derived from a ray tracing method through one or both of the person's eyes. The ray tracing method can also determine information about the optical properties of one or both of the person's eyes. The ray tracing method may be a chief-ray ray tracing method or a ray bundle ray tracing method whereas the diameter of the bundle may have the size of the pupil of he person's eye.

Optionally (e.g., instead of conducting a wavefront analysis or a ray tracing method) objective refraction may also be derived from measurement of the tomography of the respective person's eyes. The determination of the tomography of a person's eye can deliver in a first the topography of the eye and subsequently by calculation the aberration of the eye.

The subjective refraction can include determining a value for sphere of one or both of the person's eyes. This value for distinguishing reasons in the following is called first value for sphere. Additionally or alternatively the objective refraction may include determining a value for sphere of one or both of the person's eyes. This value may differ from the first value for sphere and therefore in the following is named second value of sphere. Consequently, calculating the prescription can include determining a prescription value for sphere of one or both of the person's eyes from the first value for sphere of one or both of the person's eyes and the second value for sphere of one or both of the person's eyes. This prescription value may be an average value resulting from the first and second values described above. Averaging may include different weighing of the first and second values. In a simple case the arithmetic average will be used. This prescription value may also be derived from the second value, whereas the second value has be within a certain range of the first value, otherwise it will be shifted within this range.

The subjective refraction can also include determining a first value for cylinder of one or both of the person's eyes. The objective refraction can correspondingly include determining a second value for cylinder of one or both of the person's eyes. Calculating the prescription can therefore include determining a prescription value for cylinder of one or both of the person's eyes from the first value for cylinder of one or both of the person's eyes and/or the second value for cylinder of one or both of the person's eyes. The wordings "first" and "second" are used for distinguishing reasons, only. Again, this prescription value for cylinder may be an average value resulting from the first and second values described in the foregoing. Averaging again may include different weighing of the first and second values for cylinder. This prescription value may also be derived from the second value, whereas the second value has be within a certain range of the first value, otherwise it will be shifted within this range.

In addition or as an alternative the subjective refraction can include determining a first value for cylinder axis of one or both of the person's eyes. Similarly, the objective refraction can include determining a second value for cylinder axis of one or both of the person's eyes. Calculating the prescription thus can include determining a prescription value for cylinder axis of one or both of the person's eyes from the first value for cylinder axis of one or both of the person's eyes and/or the second value for cylinder axis of one or both of the person's eyes. The prescription axis value can be an average value. Alternatively, as a prescription value the first or second axis values can be used.

In another implementation of the methods described above calculating the prescription can include determining a prescription value for mean sphere of one or both of the person's eyes from a first value for mean sphere of one or both of the person's eyes as calculated from the sum of the first value for sphere and half of the first value for cylinder and a second initial value for mean sphere of one or both of the person's eyes as calculated from the sum of the second value for sphere and half of the second value for cylinder.

Additionally or alternatively, the methods can be embellished such that a second value for mean sphere of one or both of the person's eyes is set to the sum of the second initial value for mean sphere for the respective eye and a predetermined plus value if the second initial value for mean sphere for the respective eye exceeds the predetermined plus value and wherein the second value for mean sphere for the respective eye is set to the difference of the second initial value for mean sphere for the respective eye and a predetermined minus value if the second initial value for mean sphere for the respective eye exceeds the predetermined minus value. The difference of the first mean spheres between the two eyes and the difference of the second mean spheres between the two eyes can be calculated. The method may be performed such that the second mean spheres of the respective eyes are amended such that the differences between the first and second mean spheres of the respective two eyes are identical and such that the prescription value for mean sphere of the respective eye is set to the amended second mean sphere.

A typical predetermined plus value is in the range between 0.1 and 1 dpt, e.g. between 0.15 dpt and 0.75 dpt, for example 0.25 dpt. The predetermined minus value can be set to different values dependent on the range of wanted addition. Exemplarily, the predetermined minus value can be set to: a) 0.50 dpt for a wanted addition between 0.00 dpt and 1.75 dpt; b) 0.25 dpt for a wanted addition between 2,00 dpt and 2.25 dpt; or c) 0.00dpt for a wanted addition greater than 2.25 dpt One method may include setting the prescription value for cylinder of the respective eye to the first value for cylinder of the respective eye. One method may include setting the prescription value for cylinder axis of the respective eye to the first value for cylinder axis of the respective eye.

One of the methods referred to can include that the subjective refraction includes determining a first value for an addition and/or that the objective refraction includes determining a second value for an addition.

The subjective refraction can include if necessary determining first values for prism and base. Similarly, the objective refraction can include determining second values for prism and base.

The method may include that the prescription value for prism for the respective eye is set to the first value for prism for the respective eye. Alternatively, the prescription value for base for the respective eye can be set to the first value for base for the respective eye.

For example, the information about the person's vision is information about the person's binocular and/or monocular vision.

The wavefront measurement can be made using a wavefront sensor. The wavefront sensor can be a Hartmann-Shack sensor.

Calculating the prescription can include determining a value for cylinder from the information about the optical properties of one or both of the person's eyes. Calculating the prescription can include determining a value for cylinder axis from the information about the optical properties of one or both of the person's eyes. Calculating the prescription can include determining a value for sphere from the information about the optical properties of one or both of the person's eyes. Determining the value for sphere can include determining an initial sphere value based on the information about the person's vision and adjusting the initial sphere value based on the information about the optical properties of one or both of the person's eyes.

The prescription can be calculated using an electronic processor. Outputting the prescription can include printing the prescription, displaying the prescription, or sending the prescription over an electronic network.

The methods can include ordering eyeglass lenses based on the prescription.

The methods disclosed herein can include one or more of the following advantages. In some embodiments, a person's eyeglass prescription can be obtained relatively quickly compared to conventional techniques. For example, making a wavefront measurement can provide certain information about the person's eyeglass prescription more quickly than a subjective refraction. The wavefront measurement is a relatively quick measurement (e.g., one minute or less for both eyes) compared to a conventional subjective refraction (e.g., from about 10 minutes to about 30 minutes or more). Accordingly, where information is obtained using a wavefront measurement in conjunction with a subjective refraction, the prescription can be obtained more quickly than using a subjective refraction alone. For example, in some embodiments, only binocular information about a person is obtained using subjective refraction, rather than both binocular and monocular information. Here, the monocular information can be obtained exclusively using a wavefront measurement.

In certain embodiments, a person's eyeglass prescription can be obtained more accurately compared to conventional techniques. For example, obtaining information from a wavefront measurement can provide more accurate information about a person's eyeglass prescription compared to obtaining the information using a subjective refraction. In embodiments, eyeglass prescription accuracy can be provided to an accuracy within about 0.1 dpt or less (e.g., about 0.05 dpt or less, about 0.01 dpt) for, e.g., mean sphere and/or cylinder and to an accuracy within the about 1° or less for the cylinder axis.

Prescriptions can be determined accurately with little additional input from the ECP and/or with little opportunity for the ECP to introduce human error into the eyeglass prescription. For example, the prescription can be accurately determined by a computer-implemented algorithm that operates with minimal or no input from the ECP beyond performing a wavefront measurement and subjective refraction. Accordingly, the opportunity for the ECP to introduce human error into the calculation can be the same or less as conventional techniques.

In some embodiments, the procedure used to obtain a person's eyeglass prescription can provide additional information about the person's vision without performing any additional procedures. For example, a wavefront measurement can be used to determine information about the person's night vision.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Figure 1A:
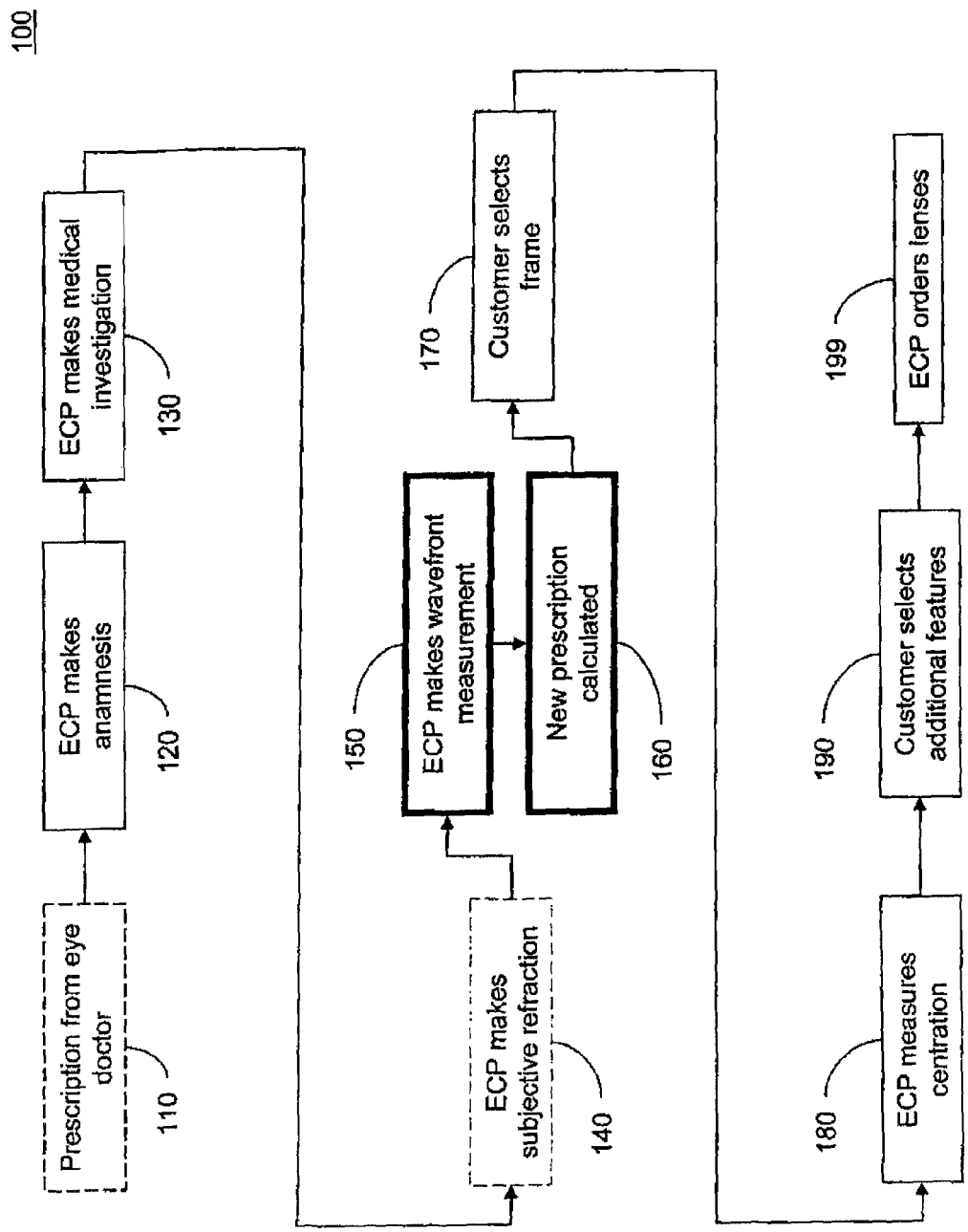
FIG. 1A is a flow chart showing a procedure for determining an eyeglass prescription of a person and ordering lenses.

Referring to FIG. 1A, a procedure 100 for obtaining an eyeglass prescription and ordering eyeglass lenses for a person includes making an anamnesis 120 and medical investigation 130 of the person, followed by a subjective refraction 140 and a wavefront measurement 150. The ECP determines a prescription 160 based on the results of subjective refraction 140 and wavefront measurement 150. After the person selects eyeglass frames 170, the ECP measures a centration 180 of the frames and orders the lenses 199 from a lens maker (e.g., from a third party lens maker or an in-house lens maker) according to the prescription 160 and centration measurement 180.

Making anamnesis 120 typically involves questioning the person regarding his or her medical and ocular history and any noticeable eye problems. Anamnesis 120 can include reviewing records of the person's eye care history. For example, in some embodiments, the anamnesis can be performed in conjunction to reviewing a previous eyeglass prescription 110.

Medical investigation 130 of a person can include determining visual acuity in each eye using the Snellen Chart, which consists of random letters of different sizes. The letters for normal vision (20/20) are ⅜-inch tall, viewed at 20 feet.

In some embodiments, medical investigation 130 include measuring the person's eye movement and peripheral vision.

These can be tested by moving a light or object through the person's field of vision and observing the person's response. The person's reaction to light (e.g., pupillary response) can also be measured.

Color blindness can be tested by, for example, having the person observe multicolored dots that form numbers. Color blindness can result in the person's inability to see certain numbers or to see a different number than people who are not color blind.

Medical investigation 130 can include glaucoma testing (e.g., tonometry), which typically involves directing a puff of air at the person's eye. The eye's response to the air puff is used to measure the pressure of the person's eyes, where abnormal readings are related to glaucoma.

Medical investigation 130 generally includes visual observation of the person's eyes by the ECP. For example, the retina, fundus, retinal vessels, and optic nerve head can be viewed with an ophthalmoscope. Drops that dilate the person's pupil may be used to allow more of the fundus to be viewed, although subjective refractive is generally performed prior to this dilation as these drops typically blur the person's vision for a period of time.

Subjective refraction 140, sometimes referred to simply as a refraction, involves positioning different lenses of different strength in front of the person's eyes using a phoropter or a trial frame and asking the person about their vision for the different lenses. Typically, the person sits behind the phoropter, and looks through it at an eye chart placed at optical infinity (e.g., 20 feet or 6 meters for distance vision), then at near (e.g., 16 inches or 40 centimeters for near vision) for individuals needing reading glasses. The ECP then changes lenses and other settings, while asking the person for subjective feedback on which settings gave the best vision. Subjection refraction is typically performed on each eye separately (monocular refraction), and then on both eyes together (binocular refraction). In certain embodiments, subjective refraction is performed only on both eyes together to provide binocular information. In such cases, the monocular information is determined from wavefront measurement 150.

Subjective refraction can be used to determine initial values for sphere (also referred to as mean sphere), cylinder, and/or cylinder axis for both eyes. This information can be determined for both distance vision and near vision.

Wavefront measurement 150 can be performed using a Hartmann-Shack sensor. In such sensors, a narrow beam of radiation output from a laser or a superluminescence diode, for example, is projected onto the retina of the person's eye through the optics of the eye. Then, radiation scattered from the retina passes through the optics, and emerges from the pupil. The wavefront of the emerging beam carries information relating to aberration errors of the optics of the eye. Then, the wavefront of the emerging beam at the exit pupil plane of the eye is relayed (by relay optics) onto a Hartmann-Shack sensor, and output from the Hartmann-Shack sensor is used to measure the wavefront of the emerging beam. For an emmetropic eye, i.e., an eye without aberration error, the wavefront of the emerging beam is a flat surface, whereas, for an eye that produces aberration errors, the wavefront of the emerging beam is distorted from the flat surface.

A Hartmann-Shack sensor typically includes a lenslet array and a CCD camera, which CCD camera is typically located at a focal plane of the lenslet array. Whenever a beam to be measured is projected onto the Hartmann-Shack sensor, the lenslet array breaks the beam into sub-apertures, and forms a pattern of focal spots. The CCD camera records this pattern of focal spots, and a computer analyzes the pattern of focal spots to measure the wavefront of the beam.

Figure 1B:
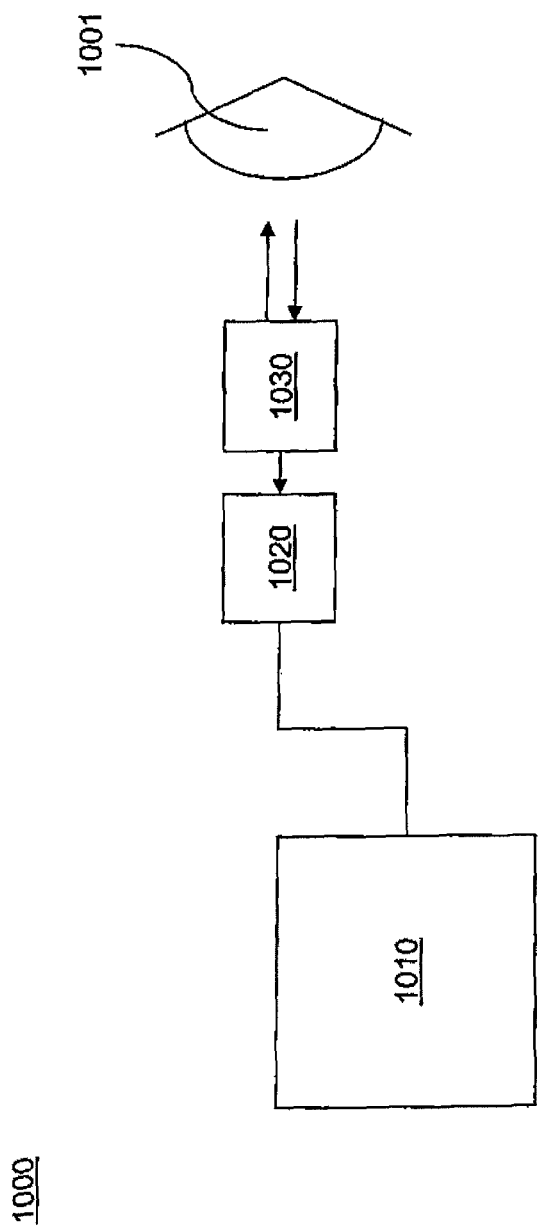
FIG. 1B is a schematic diagram of a system used to make a wavefront measurement of a person's eye and to calculate an eyeglass prescription for the person.

An exemplary system 1000 is shown in FIG. 1B. System 1000 include a relay module 1030 and a Hartman-Shack sensor 1020. Relay module 1030 illuminates a person's eye 1001 with light and collects light scattered by the retina. Relay module 1030 relays the collected light to Hartmann-Shack sensor 1020, which detects the light using a detector array (e.g., a CCD or CMOS detector array). Hartmann-Shack sensor 1020 is in communication with an electronic processor 1010 (e.g., a personal computer), which is configured to receive a signal from Hartmann-Shack sensor 1020 and determine the person's prescription from the signal based on an algorithm.

Further embodiments of methods and systems for making wavefront measurements of a people eyes are disclosed in the following patents: U.S. Pat. No. 6,382,795 B1, entitled "METHOD AND APPARATUS FOR MEASURING REFRACTIVE ERRORS OF AN EYE;" U.S. Pat. No. 6,406,146 B1, entitled "WAVEFRONT REFRACTOR SIMULTANEOUSLY RECORDING TWO HARTMANN-SHACK IMAGES;" U.S. Pat. No. 6,575,572 B2, entitled "METHOD AND APPARATUS FOR MEASURING OPTICAL ABERRATIONS OF AN EYE;" U.S. Pat. No. 6,997,555 B2, entitled "METHOD FOR DETERMINING VISION DEFECTS AND FOR COLLECTING DATA FOR CORRECTING VISION DEFECTS OF THE EYE BY INTERACTION OF A PATIENT WITH AN EXAMINER AND APPARATUS THEREFORE;" and U.S. Pat. No. 7,084,986 B2, entitled "SYSTEM FOR MEASURING THE OPTICAL IMAGE QUALITY OF AN EYE IN A CONTACTLESS MANNER." The entire contents of U.S. Pat. Nos. 6,382,795 B1, 6,406,146 B1, 6,575,572 B2, 6,997,555 B2, and 7,084,986 B2 are hereby incorporated herein by reference.

The wavefront refractor can measure a variety of different optical errors of the person's eyes, such as, for example, second order aberrations, defocus, astigmatism, and higher order aberrations including coma, trefoil, and spherical aberrations. These errors can be measured quickly (e.g., in seconds).

The person's prescription is determined based on the results of subjective refraction 140 and wavefront measurement 150 using an algorithm that can be implemented, for example, using a computer or an equivalent electronic processing device. In general, the algorithm can utilize data from a number of different sources to calculate the person's prescription. For example, in certain embodiments, the algorithm takes into account the wavefront data from both eyes, the data from subjective refraction 140 from both eyes, and additional data from the ECP. Additional data can include, for example, addition, prism, and/or base for one or both eyes, design preferences, and/or expected light conditions for the use one or both lenses. Another example of additional data is where the ECP wants the prescription to be optimized for a certain distance (e.g., different from infinity), this information can be provided so that subsequent determinations are performed based on the distance.

In general, the person's prescription can be determined from wavefront data by first determining Zernike coefficients which characterize the aberrations in the person's eye. Alternatively, or additionally, the person's prescription can be calculated from the three-dimensional wavefront map itself. The person's prescription (e.g., sphere, cylinder, and cylinder axis) can be determined from the Zernike coefficients or from the three-dimensional map using a variety of methods. For example, one can calculate sphere, cylinder, and cylinder axis by fitting a torical surface to the wavefront data. Alternatively, or additionally, the Zernike coefficients or the three-dimensional wavefront map can be used to construct an image of a point source on the person's retina, and the sphere, cylinder, and cylinder axis can be determined using an image quality metric.

Exemplary methods are disclosed, for example, in U.S. Pat. No. 6,511,180, entitled "DETERMINATION OF OCULAR REFRACTION FROM WAVEFRONT ABERRATION DATA AND DESIGN OF OPTIMUM CUSTOMIZED CORRECTION," and in European Patent No. EP 1 324 689 B1, entitled "DETERMINATION OF OCULAR REFRACTION FROM WAVEFRONT ABERRATION DATA," the entire contents both of which is hereby incorporated by reference.

In some embodiments, the person's prescription is determined from wavefront data using ray tracing techniques. For example, a ray tracing algorithm can be used to trace a bundle of rays through the patient's eye based on the wavefront data. Sphere, cylinder, and cylinder axis, for example, can be determined from the behavior of the rays at various locations along their path using one or more metrics. For example, in some embodiments, the prescription is determined using a metric based on characteristics of the bundle of rays at and around their point of minimum aperture (e.g., at their position of focus within the eye). These characteristics can include the cross-sectional area, cross-sectional shape, and/or longitudinal extension at this position.

Figure 2:
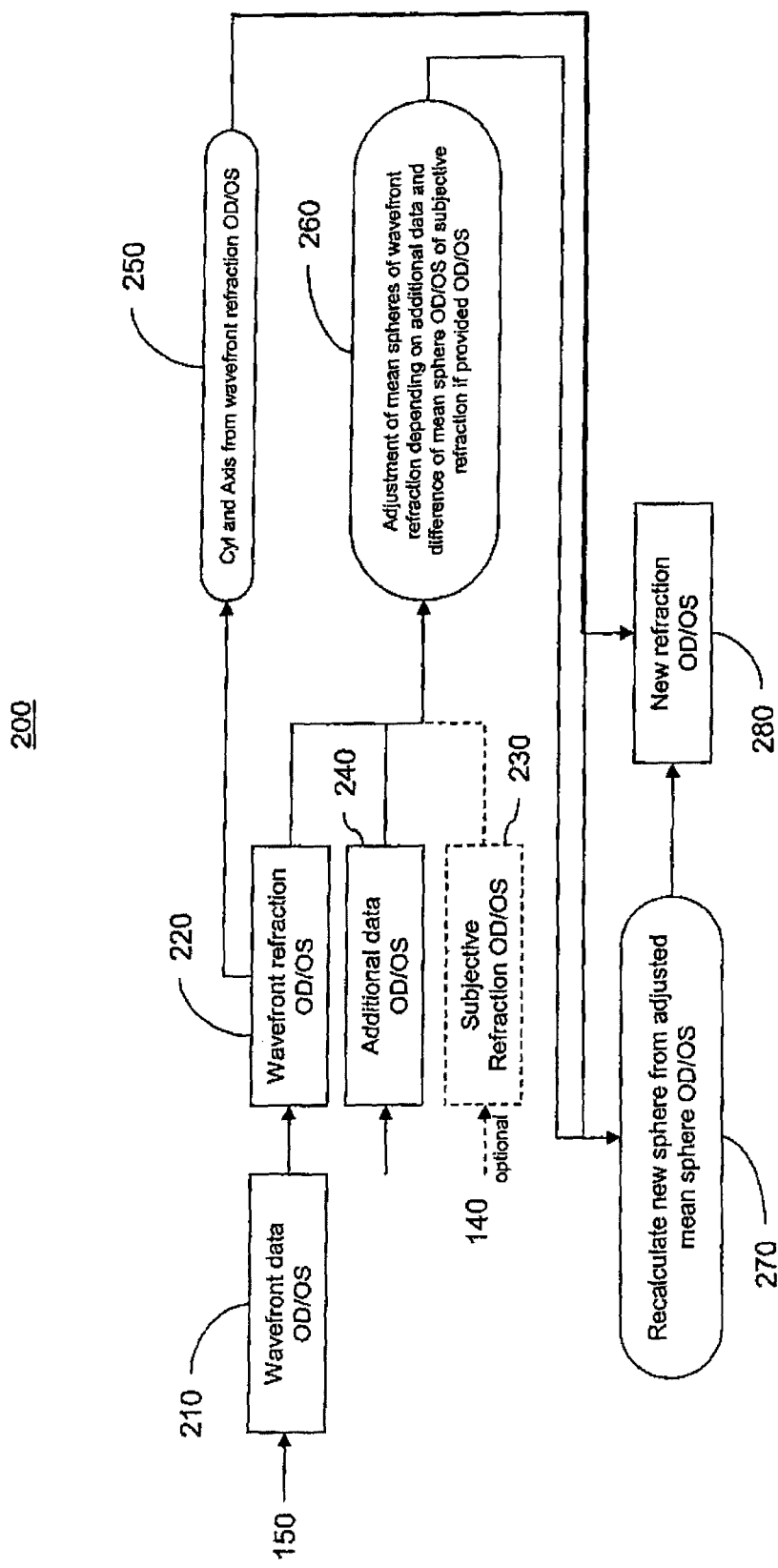
FIG. 2 is a flow chart showing a procedure for determining an eyeglass prescription of a person based on a wavefront measurement.

FIG. 2 shows a flowchart of an exemplary embodiment of an algorithm for calculating a person's eyeglass prescription. Initially, wavefront data (210) for each eye, provided by wavefront measurement 150, is used to determine a wavefront refraction for each eye (220). This involves the use of an appropriate metric on the wavefront data. The metric depends on the wavefront data, the subjective refraction (if provided) and/or the additional data. Wavefront refraction data for each eye is used to determine a cylinder and cylinder axis for each eye (250). The cylinder refers to a cylindrical deviation from a spherical lens that part of a person's prescription, usually used to correct for astigmatism. The cylinder axis refers to the relative orientation of the cylinder for each eye. Concurrently to determining the cylinder and cylinder axis, the mean spheres of wavefront refraction for each eye is adjusted (260) based on the wavefront refraction data, subjective refraction data 230 and/or additional data 240 for each eye. For example, if ECP had to adjust the mean sphere ascertained from subjective refraction 140 for one eye, this adjustment can be emulated by adjusting the wavefront refractive mean sphere of the other eye by a certain amount the difference between the mean sphere for the left eye is the same as the right eye as calculated from subjective refraction 140 is the same as the difference calculated from wavefront refraction 150.

Once appropriate mean sphere adjustments are calculated, new mean sphere values are determined from the adjustments (270). The adjusted mean sphere values are combined with the cylinder and cylinder axis calculated in 250 to determine the prescription for the person (280).

In general, the person's eyeglass prescription can be determined to a high level of accuracy using the procedures presented herein. For example, spherical and cylinder can be determined to within about 0.25 dpt or less (e.g., about 0.1 dpt or less, about 0.05 dpt or less, 0.01 dpt or less). Cylinder axis can be determined to within about ±5° or less (e.g., about ±4° or less, about ±3° or less, about ±2° or less, ±1° or less).

Referring again to FIG. 1A, as discussed previously, once the person selects eyeglass frames, the ECP performs a centration measurement 180. Centration refers to determining the horizontal distance between the centration points of the pair of lenses. This may be specified by monocular values, measured from the assumed centreline of the bridge of the nose or spectacle frame. Alternatively, if an inter-pupillary distance is specified, this is taken to be the centration distance.

In certain embodiments, the person can select addition features for the eye glasses as indicated by 190 in the flow chart of FIG. 1A. These features can include, for example, optional optical coatings (e.g., antireflection coatings), bifocal lenses, and/or sun-activated tints.

After all selections have been made, the ECP orders the lenses (199) from, e.g., a third party or in-house lens maker.

Of course, while FIG. 1A shows a specific order in procedure 100, in general, the order of can vary. For example, frame selection 170 and feature selection 190 can occur at any stage in the procedure. Furthermore, in certain embodiments, the ECP can make wavefront measurement 150 before making subjective refraction 140.

In some embodiments, wavefront measurement 150 can provide additional information about the person's vision. For example, wavefront measurement 150 can be used to provide information about the person's night vision. Furthermore, a corneal topography measurement can be made concurrently to the wavefront measurement 150, in order to determine additional information about the refractive status of the eye, which can also be used in the calculation of the eyeglass prescription. The topographic information can also be used, for example, to dispense contact lenses.

The additional information (e.g., about night vision) can be obtained from the same wavefront measurement used to obtain prescription information. Accordingly, this information can be obtained without further stressing or inconveniencing the person.

Figure 3:
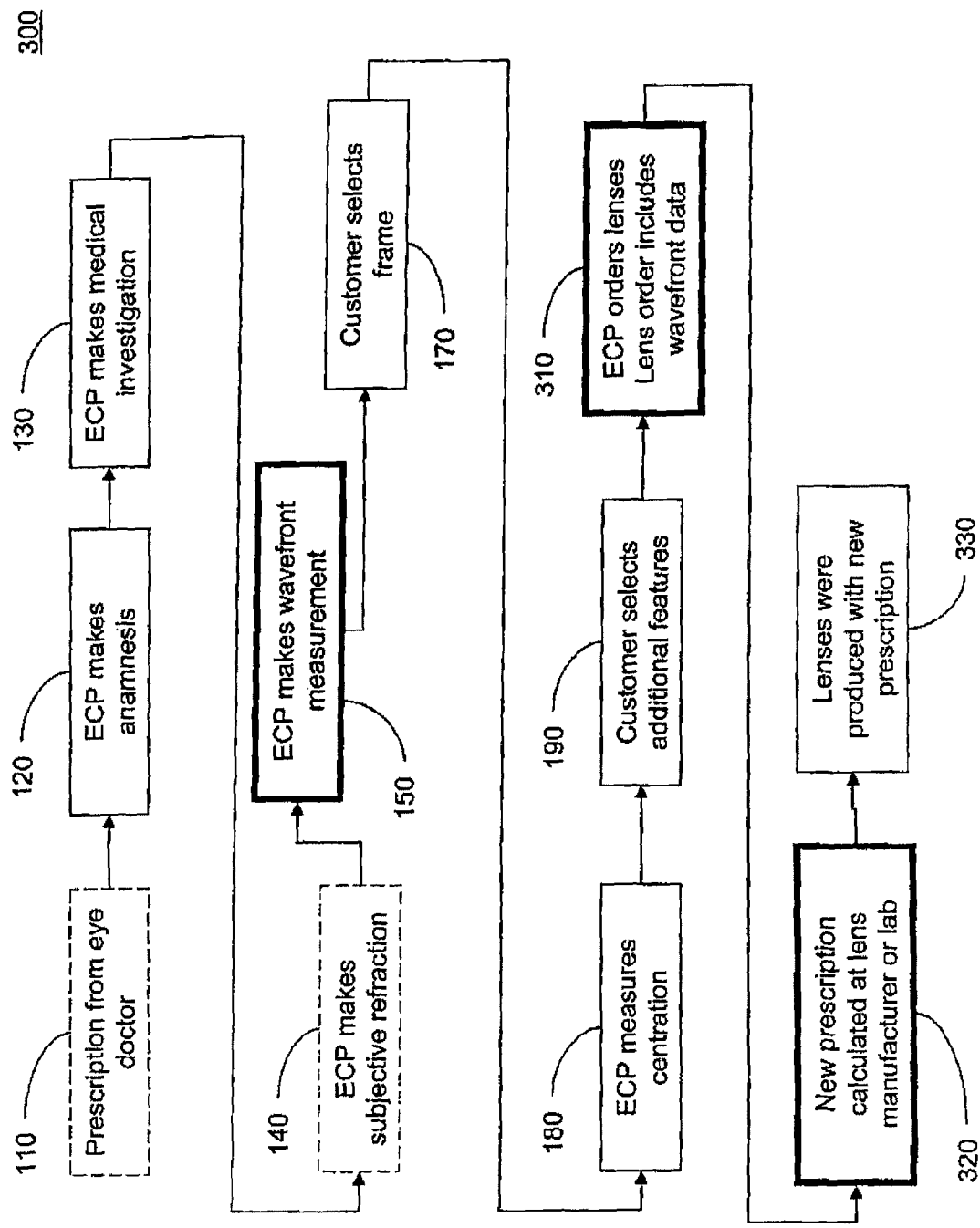
FIG. 3 is a flow chart showing a procedure for determining an eyeglass prescription of a person and ordering lenses.

In certain embodiments, certain steps in the procedure for obtaining an eyeglass prescription and ordering eyeglass lenses can be performed by people other than the ECP. For example, referring to FIG. 3, in a procedure 300, rather than determining the prescription herself, the ECP submits the results of the wavefront measurement along with other information to the lens manufacturer or laboratory (310). According to 320, the lens manufacturer or laboratory then calculate the person's prescription based on the wavefront measurement data and other information from the ECP. Finally, the lenses are manufactured based on the prescription (330). In embodiments where 320 is performed by the lens manufacturer, the manufacturer uses the prescription to make the person's lenses. In embodiments where a laboratory calculates the prescription, the lab technician submits the prescription to the lens manufacturer who makes the lenses.

In the following exemplarily the method as shown in FIG. 2 is demonstrated in a stepwise manner:

1) In a first step the wavefront data for both eyes of a patient are measured.
2) Out of these data, in a second step the wavefront refraction, namely sphere S_WR_OD/OS, cylinder C_WR_OD/OS and axis A_WR_OD/OS as the case may be for both eyes are calculated with an appropriate metric. An appropriate metric can be for example the Strehl ratio of the ocular point spread function. In the following S is an abbreviation for sphere, C is an abbreviation for cylinder and A is an abbreviation for cylinder axis. WR indicates wavefront refraction. OD and OS are abbreviations for Oculus dexter (latin for the right eye) and Oculus Sinister (latin for the left eye)
3) In a third step a subjective refraction for both eyes is made. As the case may be sphere S_SR_OD/OS, cylinder C_SR_OD/OS and axis A_SR_OD/OS are determined. If needed any addition ADD_SR, prism PR_SR_OD/OS and base BAS_SR_OD/OS; respectively, are included in the subjective refraction measurement.

4) The mean spheres MS_SR_OD, MS_SR_OS, MS_WR_OD, MS_WR_OS of all the two refractions for both eyes are calculated (sphere+half of the cylinder) in a fourth step.

5) In a fifth step a balancing of subjective and wavefront refraction is accomplished in the following manner:

If the mean spheres MS_WR_OD/OS of the wavefront refraction is more than a predetermined value (a typical value may be 0.25 dpt) more plus than the mean spheres MS_SR_OD/OS of the subjective refraction (per eye), then the mean sphere MS_WR_OD/OS of the wavefront refraction will be shifted to "mean sphere of subjective refraction MS_SR_OD/OS+this predetermined value (e.g. 0.25 dpt)":

IF $MS\_WR\_OD/OS > MS\_SR\_OD/OS + 0.25$ dpt

THEN $MS\_WR\_OD/OS = MS\_SR\_OD/OS + 0.25$ dpt (1)

6) If the mean spheres MS_WR_OD/OS of the wavefront refraction is more than a predetermined value LIMIT more minus than the mean spheres MS_SR_OD/OS of the subjective refraction (per eye), then the mean sphere MS_WR_OD/OS of the wavefront refraction will be shifted to "mean sphere of subjective refraction MS_WR_OD/OS—predetermined value LIMIT".

The predetermined value LIMIT is depending on the wanted addition ADD_SR (which is the addition ADD_SR measured at the subjective refraction in step 3)) of the lens. For addition ADD_SR 0 to 1.75, the predetermined value LIMIT is 0.5 dpt, for addition ADD_SR 2.00 to 2.25, the predetermined value LIMIT is 0.25 dpt and if the addition ADD_SR is greater than 2.25, the predetermined value LIMIT is 0. Thus, the following relationships hold:

IF $MS\_WR\_OD/OS < MS\_SR\_OD/OS - \text{LIMIT}$

THAEN $MS\_WR\_OD/OS = MS\_SR\_OD/OS - \text{LIMIT}$ (2)

wherein the LIMIT-value is determined dependent on the wanted addition ADD SR according to the following table:

TABLE 1

| Wanted addition ADD SR | Value LIMIT |
|---|---|
| 0.00 dpt to 1.75 dpt | 0.50 dpt |
| 2.00 dpt to 2.25 dpt | 0.25 dpt |
| Greater 2.25 dpt | 0.0 dpt |

7) In a seventh step the difference D_MS_SR of the mean spheres MS_SR_OD, MS_SR_OS of the subjective refraction between the two eyes is calculated:

$D\_MS\_SR = MS\_SR\_OD - MS\_SR\_OS.$ (3)

8) In the following eighth step the difference D_MS_WR of the mean spheres MS_WR_OD, MS_WR_OS of the wavefront refraction between the two eyes is calculated:

$D\_MS\_WR = MS\_WR\_OD - MS\_WR\_OS$ (4)

9) The mean spheres MS_WR_OD/OS of the wavefront refraction of the two eyes is now shifted in a ninth step to achieve the same difference D_MS_WR, D_MS_SR between the two eyes than the mean spheres of the subjective refraction MS_SR_OD/OS between the both eyes has.

Change MS_WR_OD and MS_WR_OS to achieve
$D\_MS\_WR = D\_MS\_SR$ (5)

10) Out of the new mean spheres MS_WR_OD, MS_WR_OS, the values for sphere NS_WR_OD/OS of the prescription and the cylinder C_WR_OD/OS are calculated for both eyes.

11) If the subjective refraction shows any need of an addition, this measured addition ADD_SR has to be shifted, depending on the difference $D\_MS = (MS\_SR\_OD + MS\_SR\_OS)/2 - (WR\_OD - MS\_WR\_OS)/2$ (6)

according to the following equation:

$N\_ADD = ADD\_SR + ADD\_SHIFT$ (7)

whereby the value ADD_SHIFT has to be extracted from the following table:

TABLE 2

| addition from subjective refraction ADD_SR | mean sphere difference D_MS | Predetermined shift value ADD_SHIFT |
|---|---|---|
| 0.00 dpt | +0.25 dpt to −0.50 dpt | 0.00 dpt |
| 0.75 dpt to 1.75 dpt | +0.25 dpt to +0.12 dpt | −0.25 dpt |
|  | +0.13 dpt to −0.12 dpt | 0.00 dpt |
|  | −0.13 dpt to −0.37 dpt | +0.25 dpt |
|  | −0.38 dpt to −0.50 dpt | +0.50 dpt |
| 2.00 dpt to 2.25 dpt | +0.25 dpt to +0.12 dpt | −0.25 dpt |
|  | +0.13 dpt to −0.12 dpt | 0.00 dpt |
|  | −0.13 dpt to −0.25 dpt | +0.25 dpt |
| Greater 2.25 dpt | 0.00 dpt | 0.00 dpt |

12) The final prescription consists of the new sphere NS_WR_OD/OS, the cylinder of the wavefront refraction C_WR_OD/OS, the axis of the wavefront refraction A_WR_OD/OS and if needed the additional parameters addition N_ADD, prism PR_SR_OD/OS, and base BAS_SR_OD/OS The exemplary method described above may be summarized as follows:

i) The mean spheres of the wavefront refraction is limited to the mean spheres of the subjective refraction; steps 1) to 6)

ii) The spheres of the wavefront refraction is shifted to achieve the balancing of the subjective refraction; steps 7) to 10)

iii) The addition is adjusted if needed; step 11)

iv) Cylinder and axis are taken from the wavefront refraction without any changes; step 12). In certain embodiments, the cylinder and the axis might be changed.

v) Prism and Base were taken from the subjective refraction without any changes; step 12). In some embodiments, the prism and the base might be changed.

The foregoing provides certain illustrative embodiments. Other embodiments are in the claims.

What is claimed is:

1. A method, comprising:

making a wavefront measurement of one or both of the person's eyes to determine information about the optical properties of one or both of the person's eyes;

calculating a prescription for the person comprising a corresponding value for at least one parameter for one or both of the person's eyes based on the information about the optical properties of one or both of the person's eyes, wherein calculating the prescription comprises ray tracing light paths through one or both of the person's eyes based on the information about the optical properties of one or both of the person's eyes, determining an initial value for the at least one parameter for one or both of the person's eyes based on the ray tracing, and determining the corresponding value for the at least one parameter based on a comparison of the initial value for the at least one parameter and another value for the at least one parameter obtained from a subjective refraction of one or both of the person's eyes, wherein the at least one parameter is selected from the group consisting of sphere, cylinder, axis, addition, prism, and base; and outputting the prescription.

2. A system, comprising:
relay optics configured to collect illumination scattered from a person's eye during operation of the system;
an optical sensor configured to detect the illumination collected by the relay optics; and
an electronic processor configured to receive information about the illumination detected by the optical sensor and to calculate a prescription for the person based on the information, wherein calculating the prescription comprises ray tracing light paths through the person's eye to determine a corresponding value for at least one parameter for one or both of the person's eyes based on the information, determining an initial value for the at least one parameter for one or both of the person's eyes based on the ray tracing, and determining the corresponding value for the at least one parameter based on a comparison of the initial value for the at least one parameter and another value for the at least one parameter obtained from a subjective refraction of one or both of the person's eyes,
wherein the at least one parameter is selected from the group consisting of sphere, cylinder, axis, addition, prism, and base.

3. The method of claim 1, further comprising making a subjective refraction of one or both of the person's eyes to determine the information about the optical properties of one or both of the person's eyes.

4. The method of claim 3, wherein making the subjective refraction comprises determining a value for sphere for a first eye of the person based in part on a value for sphere for a second eye of the person.

5. The method of claim 1, further comprising determining a value for sphere for a first eye of the person based in part on a value for sphere for a second eye of the person to determine information about both of the person's eyes.

6. The method of claim 1, comprising making a wavefront measurement of both of the person's eyes to determine information about the optical properties of both of the person's eyes.

7. The method of claim 6, further comprising making a subjective refraction of both of the person's eyes to determine the information about the optical properties of both of the person's eyes.

8. The method of claim 7, wherein making the subjective refraction comprises determining a value for sphere for a first eye of the person based in part on a value for sphere for a second eye of the person.

9. The method of claim 1, further comprising determining an initial sphere value based on information about the person's vision, and adjusting the initial sphere value based on the information about the optical properties of one or both of the person's eyes.

10. The method of claim 1, making the wavefront measurement comprises using at least one method selected form the group consisting of the Shack-Hartmann method and the Tscherning method.

11. The method of claim 1, further comprising making a subjective refraction of a person to determine information about the person's vision, and using the information about the person's vision to calculate the prescription.

12. The method of claim 11, wherein the information about the person's vision is information about the person's binocular vision.

13. The method of claim 1, further comprising determining a value for cylinder from the information about the optical properties of one or both of the person's eyes.

14. The method of claim 1, further comprising determining a value for cylinder axis from the information about the optical properties of one or both of the person's eyes.

15. The method of claim 1, wherein outputting the prescription comprises printing the prescription.

16. The method of claim 1, wherein outputting the prescription comprises displaying the prescription.

17. The method of claim 1, wherein outputting the prescription comprises sending the prescription over an electronic network.

18. The system of claim 2, wherein the electronic processor is configured to output the prescription.

19. The system of claim 18, wherein outputting the prescription comprises printing the prescription, displaying the prescription, and/or sending the prescription over an electronic network.

20. A method, comprising:
making a wavefront measurement of one or both of the person's eyes to determine information about the optical properties of one or both of the person's eyes; and
calculating a prescription for the person comprising a corresponding value for at least one parameter for one or both of the person's eyes based on the information about the optical properties of one or both of the person's eyes, wherein calculating the prescription comprises ray tracing light paths through one or both of the person's eyes based on the information about the optical properties of one or both of the person's eyes, determining an initial value for the at least one parameter for one or both of the person's eyes based on the ray tracing, and determining the corresponding value for the at least one parameter based on a comparison of the initial value for the at least one parameter and another value for the at least one parameter obtained from a subjective refraction of one or both of the person's eyes, wherein the at least one parameter is selected from the group consisting of sphere, cylinder, axis, addition, prism, and base.

21. The method of claim 1, wherein the ray tracing comprises tracing a bundle of rays through the one or both eyes based and calculating the prescription based on a behavior of the rays at various locations along a path of the rays using one or more metrics.

22. The method of claim 21, wherein the one or more metrics comprise a metric based on a characteristic of the bundle of rays at and around their point of minimum aperture.

23. The method of claim 22, wherein the characteristic comprises at least one of a cross-sectional area, a cross-sectional shape, and a longitudinal extension at the point of minimum aperture.

* * * * *

UNITED STATES PATENT AND TRADEMARK OFFICE
CERTIFICATE OF CORRECTION

| | |
|---|---|
| PATENT NO. | : 9,055,890 B2 |
| APPLICATION NO. | : 13/302529 |
| DATED | : June 16, 2015 |
| INVENTOR(S) | : Jesús-Miguel Cabeza-Guillén and Timo Kratzer |

It is certified that error appears in the above-identified patent and that said Letters Patent is hereby corrected as shown below:

In the specification

Col. 3, line 43, delete "he" and insert -- the --.

Col. 10, line 61, delete "eye)" and insert -- eye). --.

Col. 11, line 37, delete "THAEN" and insert -- THEN --.

Signed and Sealed this
Fifteenth Day of December, 2015

Michelle K. Lee
*Director of the United States Patent and Trademark Office*